United States Patent [19]

Miyamoto et al.

[11] Patent Number: 5,041,580

[45] Date of Patent: Aug. 20, 1991

[54] BINUCLEAR PLATINUM COMPLEX AND ANTITUMOR AGENT COMPRISING THIS COMPLEX AS ACTIVE INGREDIENT

[75] Inventors: Ken Miyamoto, Tokyo; Yuichi Fujii, Ibaraki, both of Japan

[73] Assignee: Tsumura & Co., Tokyo, Japan

[21] Appl. No.: 555,485

[22] PCT Filed: Dec. 28, 1989

[86] PCT No.: PCT/JP89/01327

§ 371 Date: Aug. 3, 1990

§ 102(e) Date: Aug. 3, 1990

[87] PCT Pub. No.: WO90/07514

PCT Pub. Date: Jul. 12, 1990

[30] Foreign Application Priority Data

Dec. 29, 1988 [JP] Japan .................................. 63-335306
Sep. 25, 1989 [JP] Japan .................................. 1-246570

[51] Int. Cl.$^5$ .............................................. C07F 15/00
[52] U.S. Cl. ...................................... 556/137; 556/136
[58] Field of Search ................ 556/137, 136; 514/492; 546/8

[56] References Cited

U.S. PATENT DOCUMENTS

| | | | |
|---|---|---|---|
| 4,533,502 | 8/1985 | Rochon et al. | 556/137 X |
| 4,560,782 | 12/1985 | Papageorgiou et al. | 556/137 |
| 4,565,884 | 1/1986 | Andrulis, Jr. et al. | 556/137 |
| 4,730,069 | 3/1988 | Kolar et al. | 556/137 |
| 4,797,393 | 1/1989 | Farrell et al. | 556/137 X |

OTHER PUBLICATIONS

Stewart et al, "Bis(Monobromoacetato)1,2-Diamino Cyclohexane Platinum(II)", *Jrnl of Clinical Hematology and Oncology*, vol. 7, No. 4, pp. 867–876, (1977).

Kidani et al, "Antitumor . . . Complexes of 1,2 Cyclohexanediamine Isomers", *Gann*, vol. 69, No. 2, pp. 263–265, (1978).

*Primary Examiner*—Arthur C. Prescott
*Attorney, Agent, or Firm*—Burns, Doane Swecker & Mathis

[57] ABSTRACT

Disclosed are a binuclear platinum complex including di-μ-sulfoacetato-bis[1,2-diaminocyclohexane-platinum (II)] and isomers thereof, and an antitumor agent comprising this complex as an effective ingredient.

This complex has a high antitumor activity and lower adverse side effects such as nephrotoxicity.

8 Claims, 1 Drawing Sheet

BINUCLEAR PLATINUM COMPLEX AND ANTITUMOR AGENT COMPRISING THIS COMPLEX AS ACTIVE INGREDIENT

TECHNICAL FIELD

The present invention relates to a novel platinum complex having an antitumor activity, which is valuable as a medicine such as an antitumor agent, and to an antitumor agent comprising this complex as an active ingredient.

BACKGROUND ART

Some platinum complexes represented by cisplatin [namely, cis-diamminedichloro platinum (II)] show a prominent antitumor effect, and are applied as chemotherapeutic agents for malignant tumors to various disease cases.

Cisplatin, however, has a very strong toxicity such as nephrotoxicity, and therefore, the remedial affect of cisplatin is hindered by this strong toxicity.

Second generation platinum complexes represented by platinum (II) cis-diammine-1,1-cyclobutanedicarboxylate, carboplatin, were developed, and although the nephrotoxicity is moderated in these platinum complexes, the antitumor activity is lower than that of cisplatin.

Accordingly, the development of a chemotherapeutic agent having a toxicity lower than those of the conventional platinum complexes, and a higher antitumor effect, is desired.

DISCLOSURE OF THE INVENTION

Figure 1:
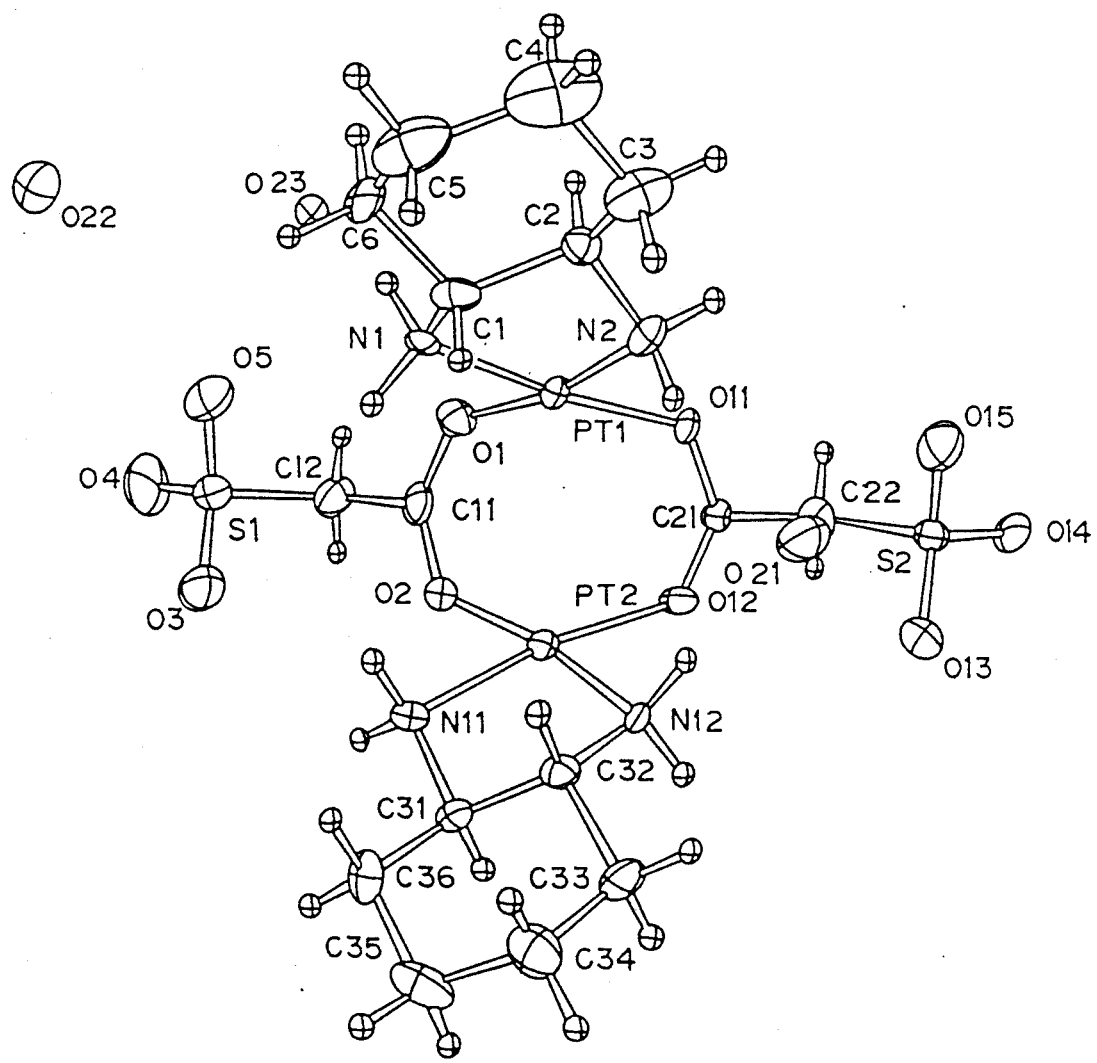
FIG. 1 is a molecular depiction of one composition within the scope of the invention; e.g. see Example 1.

The inventors carried out investigations with a view to solving the above-mentioned problem, and have proposed a novel selenious acid-platinum complex and an antitumor agent comprising this complex as an active ingredient (Japanese Patent Application No. 63-176828). After further investigations, the inventors found a novel binuclear platinum complex having a high antitumor effect, and as a result, completed the present invention.

More specifically, in accordance with the present invention, there are provided a novel binuclear platinum complex represented by the following formula I, II or III, di-μ-sulfoacetate-bis[(cis-diaminocyclohexane)-platinum (II)] and an antitumor agent comprising the platinum complex as an active ingredient:

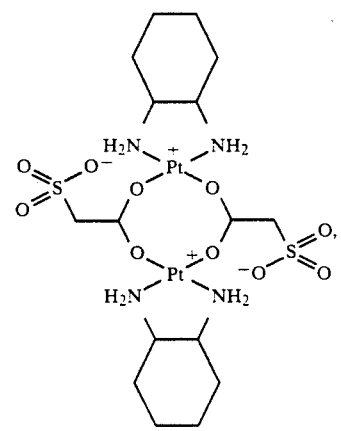

I

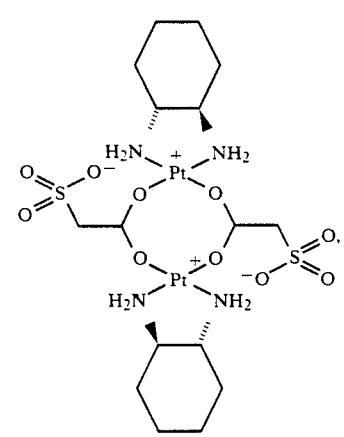

II

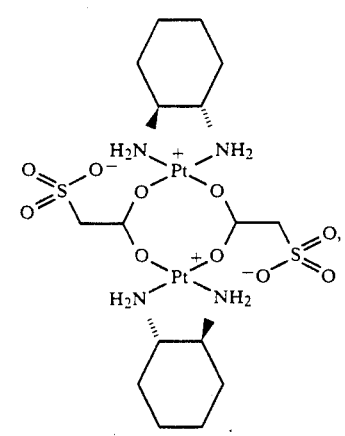

III

BEST MODE OF CARRYING OUT THE INVENTION

The novel binuclear platinum complex of the present invention (hereinafter referred to as the compound of the present invention) can be obtained, for example, in the following manner.

Namely, a dinitrato-platinum complex containing 1,2-diaminocyclohexane as the carrier ligand is used as the starting material, and the platinum complex is brought into contact with an $OH^-$ type anion exchange resin, to convert the nitrato group to a hydroxyl group, and then reacted with sulfoacetic acid.

As specific examples of the dinitrato-platinum complex, there can be mentioned dinitrato(1,2-diaminocyclohexane)platinum (II), dinitrato(1,2-diaminoethane)-platinum (II), and dinitratodiammineplatinum (II).

As the OH− anion exchange resin, there can be mentioned Diaion SA10AOH (supplied by Mitsubishi Kasei).

When the platinum complex is brought into contact with the anion exchange resin, any batch method and column method can be adopted, so long as a good contact between the resin and the platinum complex is obtained. From the viewpoint of efficiency, the column method is preferable.

For reacting the obtained reaction mixture with sulfoacetic acid, preferably sulfoacetic acid is incorporated and dissolved in the reaction mixture and the resulting mixture allowed to stand for about 30 minutes to about 2 hours. After the reaction, the solution is concentrated to precipitate a crystal, and the crystal is recovered by filtration and dried to obtain the intended compound.

In the case of the dinitrato-platinum complex valuable as the starting material of the compound of the present invention, for example, dinitrato(diaminocyclohexane)platinum (II), there are considered trans-compounds represented by dinitrato-(1R,2R)-diaminocyclohexaneplatinum (II) and dinitrato-(1S,2S)-diaminocyclohexaneplatinum (II), and cis-compounds represented by dinitrato-cis-diaminocyclohexaneplatinum (II). For the cis-compound, at least three structures including a conformer are considered.

Accordingly, the compound of the present invention includes all of isomers synthesized according to the starting material.

The antitumor effect of the compound of the present invention will now be described with reference to the following test example.

TEST EXAMPLE (antitumor effect test to mouse leukemia L1210 cells)

$1 \times 10^5$ of mouse leukemia L1210 cells were transplanted in the abdominal cavity of a 2-weeks-old male $CDF_1$ mouse, and the compound obtained in any of the examples given hereinafter was administered to the abdominal cavity three times at intervals of 4 days from the day succeeding the transplantation. Similarly, only a physiological saline solution was similarly administered in the control group.

The effect of the antitumor action was evaluated by calculating the life prolongation ratio (T/C value) from the average number of survival days in the compound-administered group and the control group according to the following formula:

$$T/C(\%) = \frac{\text{average survival day number in compound − administered group}}{\text{average survival day number in control group}} \times 100$$

The T/C values obtained in the compound-administered groups are shown in Table 1.

TABLE 1

| | Amount Administered (mg/kg) | T/C (%) |
| --- | --- | --- |
| Compound obtained in Example 1 | 25 | 128 |
| | 12.5 | 269 |
| | 6.25 | 230 |
| Compound obtained in Example 2 | 25 | 301 |
| | 12.5 | 141 |
| Compound obtained | 25 | 335 |

TABLE 1-continued

| | Amount Administered (mg/kg) | T/C (%) |
| --- | --- | --- |
| in Example 3 | 12.5 | 383 |

From the foregoing results, it was confirmed that the compound of the present invention has an excellent anti-tumor activity. During the present test, no side effects such as the nephrotoxicity were observed at all.

When the acute toxicity test of the compound of the present invention was carried out by using a mouse of the ICR line, it was found that, in the case of the administration into the abdominal cavity, the $LD_{50}$ of the compound obtained in Example 1 was 30.4 mg/kg.

Accordingly, it is understood that the compound of the present invention has an excellent antitumor activity and is valuable as a very safe antitumor agent.

The dose and preparation form of the compound of the present invention will now be described.

The compound of the present invention can be administered to animals and men directly or together with a usual pharmaceutical carrier. The administration form is not particularly critical, and an appropriate administration form can be selected according to need. Tablets, capsules, granules, fine granules and powders can be used for oral administrations, and injections and suppositories can be used for non-oral administrations.

The appropriate doses differ according to the age and body weight of a patient, and the degree of a disease, but to obtain an intended effect by an oral administration, it is considered preferable to dividedly administer the compound of the present invention in a dosage of 10 to 600 mg for an adult, several times per day.

Medicines for the oral administration are prepared by using, for example, starch, lactose, refined sugar, mannitol, carboxymethyl cellulose, corn starch, an inorganic salt and the like, by customary procedures.

In addition to the foregoing excipients, a binder, a disintegrating agent, a surface active agent, a flowability improver, a taste improver, a colorant, a perfume and the like can be used for the formation of medicines, according to need. Specific examples of these agents are described below.

Binders

Starch, dextrin, gum arabic powder, gelatin, hydroxypropyl starch, methyl cellulose, sodium carboxymethyl cellulose, hydroxypropyl cellulose, crystalline cellulose, ethyl cellulose, polyvinyl pyrrolidone, and macrogol.

Disintegrating Agents

Starch, hydroxypropyl starch, sodium carboxymethyl cellulose, calcium carboxymethyl cellulose, carboxymethyl cellulose, and lowly substituted hydroxypropyl cellulose.

Surface Active Agents

Sodium lauryl sulfate, soybean lecithin, sucrose fatty acid ester, and polysorbate 80.

Lubricants

Talc, waxes, hydrogenated vegetable oil, sucrose fatty acid ester, magnesium stearate, calcium stearate, aluminum stearate, and polyethylene glycol.

Flowability Improvers

Light silica, dry aluminum hydroxide gel, synthetic aluminum silicate, and magnesium silicate.

The compound of the present invention also can be administered in the form of a suspension, an emulsion, a syrup or an elixir. A preparation form of this type can contain a taste or smell improver and a colorant.

To obtain the intended object by a non-oral administration, it is considered preferable to administer 5 to 200 mg of the compound of the present invention per day for an adult by intravenous injection, intravenous drip, hypodermic injection or intramuscular injection.

Non-oral medicines are prepared by customary procedures and as the diluent, there are generally used distilled water for injection, physiological saline solution, an aqueous solution of glucose, a vegetable oil for injection, sesame oil, coconut oil, soybean oil, corn oil, propylene glycol, and polyethylene glycol. Furthermore, a fungicide, an antiseptic agent, and a stabilizer can be added according to need. In view of the stability, a method can be adopted in which a non-oral medicine is filled in a vial or the like and frozen, water is removed by a usual freeze-drying technique, a solution is formed from the freeze-dried product again just before administration, and the solution is then administered. Moreover, an isotonic agent, a stabilizer, an antiseptic agent, and an analgetic agent can be added according to need.

As another non-oral medicine, there can be mentioned coating agents such as an external lotion and a cream, and suppositories for rectal administration, and these non-oral medicines are prepared by customary procedures.

The present invention will now be described in detail with reference to the following examples, that by no means limit the scope of the invention.

EXAMPLE 1

In 100 ml of distilled water was dissolved under heating 4.30 g of dinitrato-(1R,2R)-diaminocyclohexaneplatinum (II) having 1,2-diaminocyclohexane as the carrier ligand, the solution was passed through a column packed with 160 ml of Diaion SA10AOH, and an elution was effected with distilled water. Then 1.40 g of sulfoacetic acid (supplied by Aldrich) was dissolved as a dissociating acid into the eluate, and the solution was heated at 60° C. for 1 hour and concentrated by a rotary evaporator. When the volume was reduced to 30 ml, the evaporation was stopped, the precipitated crystal was recovered by filtration, and the obtained solid was thoroughly washed with distilled water and air-dried to obtain a light yellow solid.

From the following physical and chemical properties thereof, this light yellow solid was identified as di-$\mu$-sulfoacetato-bis[(1R,2R)-diaminocyclohexaneplatinum (II)] trihydrate.

Yield:
3.2 g (72%)
Elementary analysis:
Calculated value: C=20.25%, H=4.04%, N=5.91%, S=6.76%
Found value: C=20.25%, H=3.93%, N=5.99%, S=6.76%
Single crystal X-ray structural analysis:
orthrhombic, molecular weight Fw=948.80
Space group:
$P2_12_12_1$
Unit lattice:
a=19.186 (4) Å
b=14.577 (2) Å
c=9.876 (1) Å
(four molecules are contained per unit lattice)
Calculated density:
$D_x$=2.28 g/cm$^3$
Measured density:
$D_m$=2.25 g/cm$^3$
R value:
0.033 (wR=0.031)
V value:
V=2762 (1) Å$^3$
Note, 2455 independent reflections were used for the structural analysis.

The molecular diagram of this compound based on the single crystal X-ray structural analysis is shown in FIG. 1.

EXAMPLE 2

A light yellow solid was prepared in the same manner as described in Example 1, except that 4.30 g of dinitrato-(1S,2S)-diaminocyclohexaneplatinum (II) having 1,2-diaminocyclohexane as the carrier ligand was used.

From the following physical and chemical properties thereof, this light yellow solid was identified as di-$\mu$-sulfoacetato-bis[(1S,2S)-diaminocyclohexaneplatinum (II)] trihydrate.

Yield:
3.2 g (72%)
Elementary analysis:
Calculated values: C=20.25%, H=4.04%, N=5.91%, S=6.76%
Found values: C=20.04%, H=4.02%, N=5.97%, S=6.57%

EXAMPLE 3

A light yellow solid was prepared in the same manner as described in Example 1, except that 4.30 g of dinitrato-cis-diaminocyclohexaneplatinum (II) having cis-diaminocyclohexane as the carrier ligand was used.

From the following physical and chemical properties thereof, this light yellow solid was identified as di-$\mu$-sulfoacetato-bis[cis-diaminocyclohexaneplatinum (II)] trihydrate.

Yield:
3.2 g (72%)
Elementary analysis:
Calculated value: C=20.25%, N=4.04%, N=5.91%, S=6.76%
Found values: C=20.42%, H=3.94%, N=5.84%, S=6.76%

EXAMPLE 4

| (1) Corn starch | 52 g |
| (2) Crystalline cellulose | 40 g |
| (3) Calcium carboxymethyl cellulose | 5 g |
| (4) Light silica | 0.5 g |
| (5) Magnesium stearate | 0.5 g |
| (6) Compound obtained in Example 1 | 2 g |
| Total | 100 g |

According to the above-mentioned recipe, components (1) through (6) were homogeneously mixed, and the mixture was compression-molded by a tableting machine to obtain tablets each having a weight of 200 mg.

Each tablet contained 4 mg of the compound obtained in Example 1, and 3 to 50 tablets were dividedly administered to an adult, several times per day.

EXAMPLE 5

| (1) Crystalline cellulose | 92.5 g |
| (2) Magnesium stearate | 0.5 g |
| (3) Calcium carboxymethyl cellulose | 5 g |
| (4) Compound obtained in Example 2 | 2 g |
| Total | 100 g |

According to the above-mentioned recipe, components (1) and (4) and a part of component (2) were homogeneously mixed, and the mixture was compression-molded and pulverized. Then component (3) and the remainder of component (2) were added to the pulverization product, and the mixture was compression-molded by a tableting machine to obtain tablets each having a weight of 200 mg.

Each table contained 4 mg of the compound obtained in Example 2, and 3 to 50 tablets were dividedly administered to an adult, several times per day.

EXAMPLE 6

| (1) Crystalline cellulose | 42.5 g |
| (2) 10% solution of hydroxypropyl cellulose in ethanol | 50 g |
| (3) Calcium carboxymethyl cellulose | 5 g |
| (4) Magnesium stearate | 0.5 g |
| (5) Compound obtained in Example 3 | 2 g |
| Total | 100 g |

According to the above-mentioned recipe, components (1), (2) and (5) were homogeneously mixed, and by customary procedures, the mixture was kneaded, granulated by an extrusion granulator, dried, and disintegrated. Then the disintegration product was mixed with components (3) and (4) and the mixture was compression-molded by a tableting machine to obtain tablets each having a weight of 200 mg.

Each tablet contained 4 mg of the compound obtained in Example 3, and 3 to 50 tablets were dividedly administered to an adult, several times per day.

EXAMPLE 7

| (1) Corn starch | 93 g |
| (2) Magnesium stearate | 0.5 g |
| (3) Calcium carboxymethyl cellulose | 5 g |
| (4) Light silica | 0.5 g |
| (5) Compound obtained in Example 1 | 1 g |
| Total | 100 g |

According to the above-mentioned recipe, components (1) through (5) were homogeneously mixed, compression-molded by a compression molding machine, pulverized by a pulverizer, and classified to obtain a granule.

This granule contained 10 mg of the compound obtained in Example 1 per gram of the granule, and 1 to 20 g of the granule was dividedly administered to an adult, several times per day.

EXAMPLE 8

| (1) Crystalline cellulose | 69 g |
| (2) 10% solution of hydroxypropyl cellulose in ethanol | 30 g |
| (3) Compound obtained in Example 2 | 1 g |
| Total | 100 g |

According to the above-mentioned recipe, components (1) through (3) were homogeneously mixed, and the mixture was kneaded, granulated by an extrusion granulator, dried, and classified to obtain a granule.

The granule contained 10 mg of the compound obtained in Example 2 per gram of the granule, and 1 to 20 g of the granule was dividedly administered to an adult, several times per day.

EXAMPLE 9

| (1) Corn starch | 97.5 g |
| (2) Light silica | 0.5 g |
| (3) Compound obtained in Example 3 | 2 g |
| Total | 100 g |

According to the above-mentioned recipe, components (1) through (3) were homogeneously mixed, and the mixture was filled in capsules No. 2 so that each capsule contained 200 mg of the mixture.

Each capsule contained 4 mg of the compound obtained in Example 3, and 3 to 50 capsules were dividedly administered to an adult, several times per day.

EXAMPLE 10

| (1) Distilled water for injection | Appropriate amount |
| (2) Glucose | 200 mg |
| (3) Compound obtained in Example 1 | 100 mg |
| Total | 5 ml |

Components (2) and (3) were dissolved in distilled water for injection, and the solution was poured in an ampoule having a capacity of 5 ml and sterilized under pressure at 121° C. for 15 minutes to obtain an injection.

We claim:

1. A binuclear platinum complex represented by the following formula I:

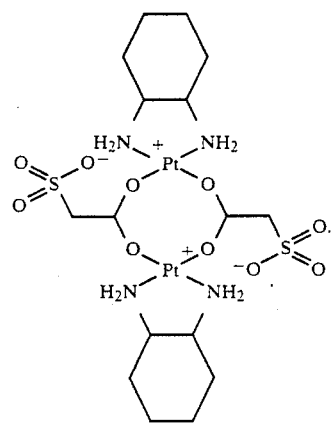

2. A binuclear platinum complex represented by the following formula II.

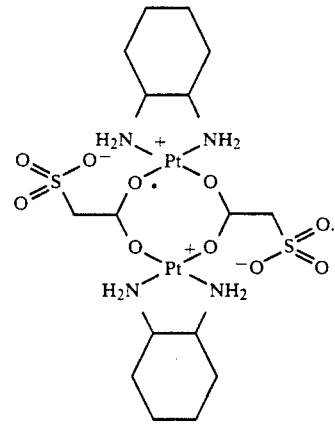

I

3. A binuclear platinum complex represented by the following formula III:

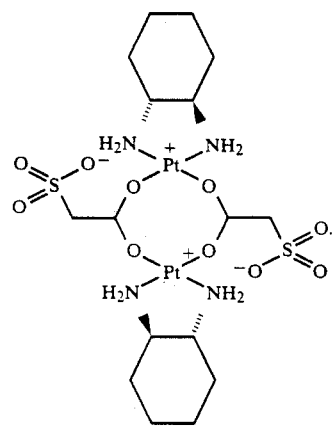

II

4. Di-μ-sulfoacetato-bis[(cis-diaminocyclohexane)-platinum (II)].

5. An antitumor agent comprising as an effective ingredient a binuclear platinum complex represented by the following formula:

6. An antitumor agent comprising as an effective ingredient a binuclear platinum complex represented by the following formula:

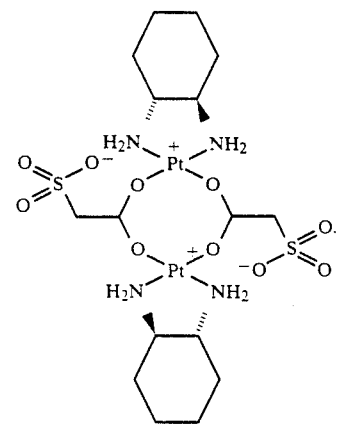

II

7. An antitumor agent comprising as an effective ingredient a binuclear platinum complex represented by the following formula:

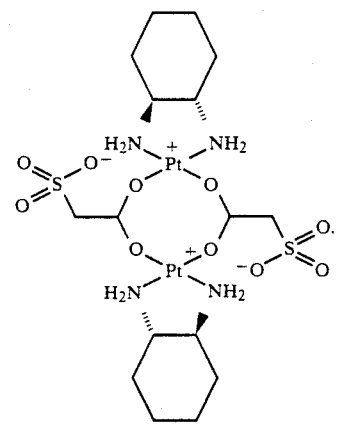

III

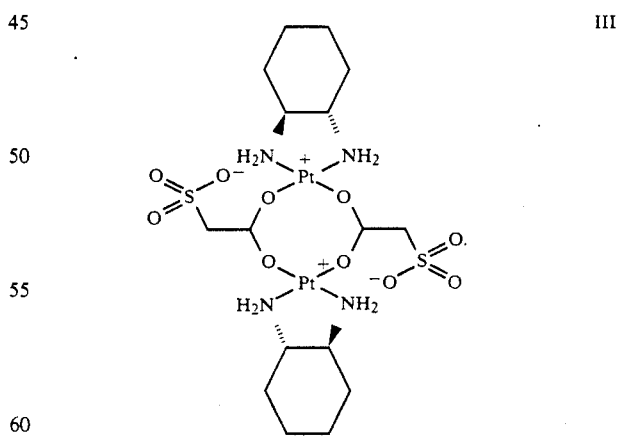

8. An antitumor agent comprising di-μ-sulfoacetato-bis-[(cis-diaminocyclohexane)platinum (II)] as an effective ingredient.

* * * * *